United States Patent
Barwicz et al.

(10) Patent No.: US 9,625,379 B2
(45) Date of Patent: Apr. 18, 2017

(54) GAS SENSOR WITH INTEGRATED OPTICS AND REFERENCE CELL

(71) Applicant: International Business Machines Corporation, Armonk, NY (US)

(72) Inventors: Tymon Barwicz, Yorktown Heights, NY (US); William M. Green, Irvington, NY (US); Yves C. Martin, Ossining, NY (US); Jason S. Orcutt, Katonah, NY (US); Lionel Tombez, Yonkers, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

(21) Appl. No.: 14/799,894

(22) Filed: Jul. 15, 2015

(65) Prior Publication Data

US 2017/0016817 A1     Jan. 19, 2017

(51) Int. Cl.
*G01N 21/00* (2006.01)
*G01N 21/39* (2006.01)
*G01N 21/3504* (2014.01)

(52) U.S. Cl.
CPC ......... *G01N 21/39* (2013.01); *G01N 21/3504* (2013.01); *G01N 2201/063* (2013.01); *G01N 2201/06113* (2013.01)

(58) Field of Classification Search
CPC ..... G01J 1/1626; G01N 21/534; G01N 21/59; G01N 21/27; G01N 21/8507
USPC ........................................................ 356/435
See application file for complete search history.

(56) References Cited

U.S. PATENT DOCUMENTS

| | | |
|---|---|---|
| 7,046,362 B2 | 5/2006 | Lehmann et al. |
| 8,005,332 B2 | 8/2011 | Schmidt et al. |
| 8,385,693 B2 | 2/2013 | Schmidt et al. |
| 8,585,974 B2 | 11/2013 | Chakravarty et al. |
| 8,636,955 B2 | 1/2014 | Chakravarty et al. |
| 8,836,327 B2 | 9/2014 | French et al. |
| 2004/0026037 A1* | 2/2004 | Shinriki ............... C23C 16/40 156/345.33 |
| 2011/0309331 A1* | 12/2011 | Yu ....................... H01L 27/1443 257/21 |
| 2013/0322813 A1 | 12/2013 | Grondin et al. |

(Continued)

OTHER PUBLICATIONS

List of IBM Patents or Patent Applications Treated as Related; (Appendix P), Filed Mar. 7, 2016; 2 pages.

(Continued)

*Primary Examiner* — Tarifur Chowdhury
*Assistant Examiner* — Md M Rahman
(74) *Attorney, Agent, or Firm* — Cantor Colburn LLP; Vazken Alexanian

(57) ABSTRACT

A method of fabricating a gas sensor on a substrate and a gas sensor fabricated on a substrate that includes optical and electronic components are described. The method includes fabricating a laser to output light over a range of wavelengths within a waveguide, fabricating a splitter to split the light output by the laser to a reference waveguide and to a detection waveguide, fabricating a reference cell to house the reference waveguide and a reference gas. An output of the reference waveguide is coupled to a first optical detector and an output of the detection waveguide is coupled to a second optical detector to identify or quantify an ambient gas.

10 Claims, 6 Drawing Sheets

(56) References Cited

U.S. PATENT DOCUMENTS

| | | | |
|---|---|---|---|
| 2014/0176958 A1* | 6/2014 | Flanders | H01S 5/06 356/479 |
| 2015/0103350 A1* | 4/2015 | Luo | G01N 21/3504 356/437 |

OTHER PUBLICATIONS

Tymon Barwicz et al., "Gas Sensor With Integrated Optics and Reference Cell", U.S. Appl. No. 15/062,353, filed Mar. 7, 2016.

Hatori et al., "A Hybrid Integrated Light Source on a Silicon Platform Using a Trident Spot-Size Converter", Journal of Lightwave Technology, vol. 32, No. 7, Apr. 1, 214, pp. 1329-1336.

Lai et al., "On-chip methane sensing by near-IR absorption signatures in a photonic crystal slot waveguide", Optics Letters, vol. 36, No. 6, Mar. 15, 2011, pp. 984-986.

Liew et al., "Microfabricated alkali atom vapor cells", Applied Physics Letters, vol. 84, No. 14, Apr. 5, 2004, pp. 2694-2696.

Nitkowski et al., "Cavity-enhanced on-chip absorption spectroscopy using microring resonators", Optics Express, vol. 16, No. 16, Aug. 4, 2008, pp. 11930-11936.

Pavone et al., "Frequency- and Wavelength-Modulation Spectroscopies: Comparison of Experimental Methods Using an AlGaAs Diode Laser", Applied Physics B, vol. 56, No. 2, Feb. 1993, pp. 118-122.

Stern et al., "Nanoscale light—matter interactions in atomic cladding waveguides", Nature Communications, vol. 4, 2013, pp. 1-7.

Straessle et al., "Low-temperature indium-bonded alkali vapor cell for chip-scale atomic clocks", Journal of Applied Physics, vol. 113, No. 6, 2013, pp. 1-8.

Straessle et al., "Microfabricated alkali vapor cell with anti-relaxation wall coating", Applied Physics Letters, vol. 105, No. 4, 2014, pp. 1-4.

Vernooy et al., "Alignment-Insensitive Coupling for PLC-Based Surface Mount Photonics", IEEE Photonics Technology Letters, vol. 16, No. 1, Jan. 2004, pp. 269-271.

List of IBM Patents or Patent Applications Treated as Related; (Appendix P), Filed Jan. 7, 2016; 2 pages.

Tymon Barwicz et al., "Gas Sensor With Integrated Optics and Reference Cell", U.S. Appl. No. 14/949,284, filed Nov. 23, 2015.

* cited by examiner

GAS SENSOR WITH INTEGRATED OPTICS AND REFERENCE CELL

BACKGROUND

The present invention relates to gas sensing, and more specifically, to a gas sensor with integrated optics and a reference cell.

Detection and identification of gas in the environment can be useful in a number of scenarios for safety and informational purposes. Some applications benefit from a small (e.g., microscale) sensor, which can offer higher sensitivity and reduced response time, for example. Gas detection and concentration measurement may be performed using the characteristic optical absorption of the gas species of interest. Based on the smaller scale, a smaller sample is needed. In particular, an on-chip optical absorption spectrometer may be used for gas detection.

SUMMARY

According to one embodiment of the present invention, a method of fabricating a gas sensor on a substrate includes fabricating a laser to output light over a range of wavelengths within a waveguide; fabricating a splitter to split the light output by the laser to a reference waveguide and to a detection waveguide; fabricating a reference cell to house the reference waveguide and a reference gas, wherein an output of the reference waveguide is coupled to a first optical detector and an output of the detection waveguide is coupled to a second optical detector to identify or quantify an ambient gas.

According to another embodiment, a gas sensor fabricated on a substrate that includes optical and electronic components includes a laser configured to output light in a range of wavelengths within a waveguide; a splitter configured to split the light output by the laser to a reference waveguide and to a detection waveguide; the reference waveguide configured to expose the light to a reference gas and output a reference light, wherein the reference light exhibits a change in intensity from the light at wavelengths corresponding with an absorption spectrum of the reference gas; a reference cell configured to hermetically seal the reference gas and house the reference waveguide; the detection waveguide configured to expose the light to ambient gas; and first and second optical detectors configured to receive light output from the reference waveguide and the detection waveguide, respectively, wherein the ambient gas is identified based on outputs of the first detector and the second detector.

Additional features and advantages are realized through the techniques of the present invention. Other embodiments and aspects of the invention are described in detail herein and are considered a part of the claimed invention. For a better understanding of the invention with the advantages and the features, refer to the description and to the drawings.

BRIEF DESCRIPTION OF THE DRAWINGS

The subject matter which is regarded as the invention is particularly pointed out and distinctly claimed in the claims at the conclusion of the specification. The forgoing and other features, and advantages of the invention are apparent from the following detailed description taken in conjunction with the accompanying drawings in which:

DETAILED DESCRIPTION

As noted above, an on-chip optical absorption spectrometer may be used for gas detection. The laser light source used by the spectrometer must emit multiple wavelengths, at least some of which are absorbed by the gas of interest and others of which pass unaffected. The light transmitted within the medium is guided in optical waveguides (e.g., nanoscale optical waveguides) and undergoes total internal reflection at the boundaries. A fraction of the light is guided in the air cladding and is referred to as an evanescent wave. The evanescent wave interacts with the gas sample to be analyzed. Based on a comparison of the transmitted light to the detected light and, thus, an identification of the absorbed wavelengths, the gas and its concentration may be identified. Embodiments of the sensors and methods detailed herein relate to an optical absorption spectrometer that includes integrated electrical and optical components and a reference gas cell. The reference gas facilitates tuning the laser wavelengths to include the absorbance wavelength of the gas of interest and also facilitates self-diagnosis of the sensor. The integration of electrical and optical components produces a sensor that may exhibit both cost and power efficiencies.

Figure 1:
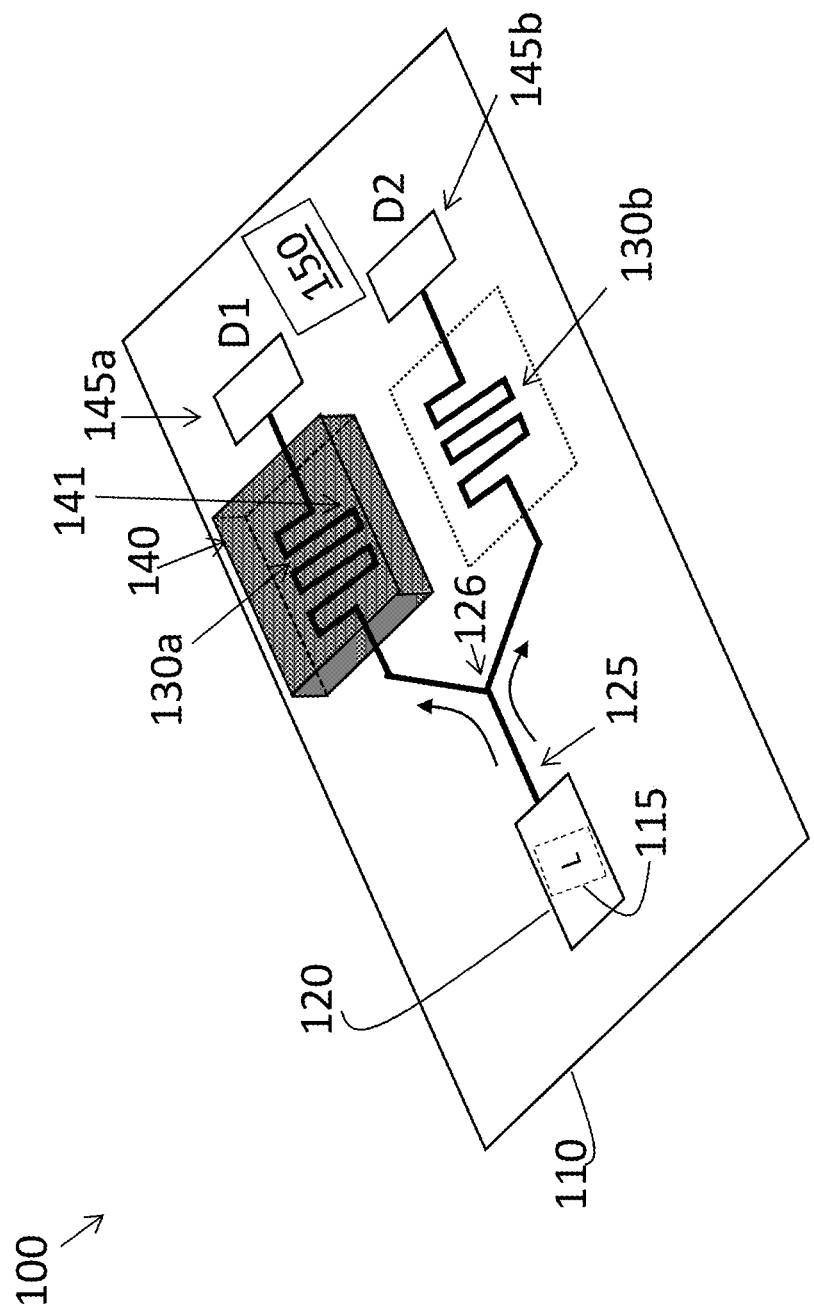
FIG. 1 is a schematic diagram of a gas sensor according to an embodiment of the invention.

FIG. 1 is a schematic diagram of a gas sensor 100 according to an embodiment of the invention. The sensor 100 is formed on a substrate 110 (e.g., silicon) that includes electronic components as well as the optical components shown. The light source is a laser (L) 115 that may be formed on a III-V substrate 120 (compound semiconductor). The laser 115 may be on the order of 1 millimeter (mm) in size and emit light on the order of a few milliwatts (mW). The laser 115 may output light in the infrared spectrum. The laser 115 may be an edge-emitting laser such that the emitted light can be directed into the waveguide 125. A splitter 126 splits the light in the waveguide 125 to a first waveguide 130*a* in a reference cell 140 and to a second waveguide 130*b*. Each of the waveguides 125, 130*a*, 130*b* may be fabricated from a transparent material such as, for example, glass or pure silicon, which is transparent for radiations (e.g., infrared radiation). Thus, the light from the edge-emitting laser 115 stays in the line (e.g., within the waveguide 125) or other shape formed by the pure silicon or glass, for example. The evanescent wave of each of the waveguides 130*a*, 130*b* interacts with the reference gas (in the reference cell) and the environment, respectively. The shape of the waveguides 130*a*, 130*b* (e.g., serpentine) extends the time of exposure of the light from the laser 115 to the reference gas 141 (in the reference cell 140) or to the environment. The reference cell 140 is hermetically sealed as further discussed below. The incident light into the waveguides 130*a*, 130*b* (light emitted by the laser 115) includes a set of wavelengths at an initial intensity. The output of each waveguide 130*a*, 130*b* may be light with a different intensity at one or more of the wavelengths than the incident light output by the laser 115 because of the absorptive effect of the reference gas 141 (in the case of waveguide 130a) or gas in the environment (in the case of waveguide 130b). The wavelengths that exhibit the change in intensity are associated with the identity and concentration of the gas (reference gas 141 in the case of the output of waveguide 130a and gas in the environment in the case of the output of waveguide 130b). The outputs of each of the waveguides 130a, 130b are received at respective detectors (D1 and D2) 145a, 145b. Each detector 145a, 145b may be an integrated photodiode that converts received light to an electrical signal. When the reference gas 141 (in the reference cell 140) is the gas of interest, a straight-forward comparison of the electrical signal output by each of the two detectors 145a, 145b may be sufficient to indicate whether the gas of interest is present in the environment. Alternatively, signal processing may be performed on the detector 145a, 145b outputs. The electronic components may include a processor 150 that processes outputs from the detectors 145a, 145b to identify the gas 141 as well as determine its concentration.

Figure 2:
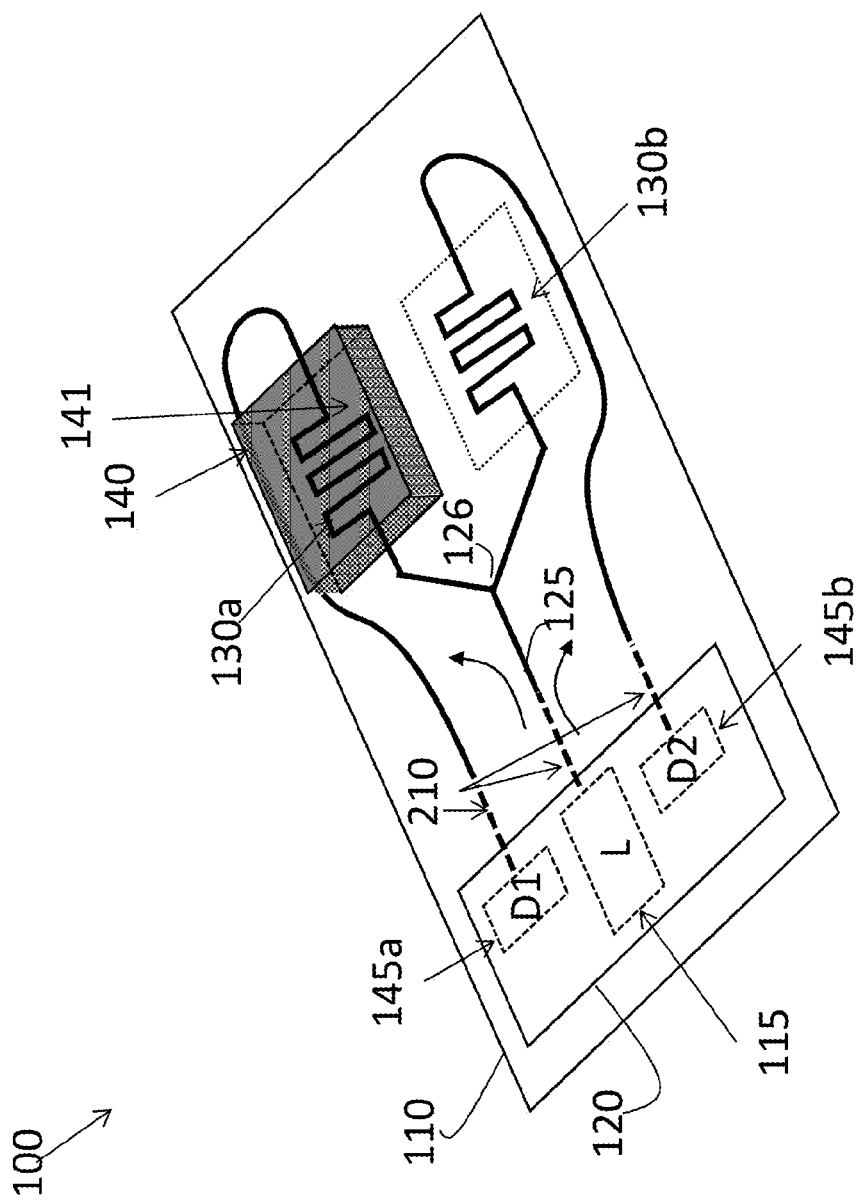
FIG. 2 is a schematic diagram of a gas sensor according to an embodiment of the invention.

FIG. 2 is a schematic diagram of a gas sensor 100 according to an embodiment of the invention. In the embodiment shown in FIG. 2, the detectors 145a, 145b, in addition to the laser 115, may be formed on the III-V substrate 120. The III-V substrate 120 may be a gallium arsenide (GaAs) or indium phosphide (InP) substrate, for example. The laser 115 and detectors 145a, 145b formed on the III-V substrate 120 require less power than those formed on a different type of substrate. As discussed with reference to FIG. 1, the laser 115 outputs light to the waveguide 125. This light is split by the splitter 126 to the waveguide 130a in the reference cell 140, where the light is exposed to the reference gas 141, and to the waveguide 130b wherein the light is exposed to the environment. The output from the waveguides 130a, 130b is routed back to the III-V substrate 120 to the respective detectors 145a, 145b. Because of the arrangement of the embodiment shown in FIG. 2, optical couplers 210 are used to transition the optical signal (from the laser 115 and from the waveguides 130a, 130b) between the III-V substrate 120 and the (silicon) substrate 110. The optical couplers 210 are high-transmission low-reflection interfaces. Exemplary optical couplers 210 include a spot size converter and adiabatic coupler. The spot size converter is a known optical coupler 210 that provides a butt junction interface (through the use of spot-size converters) between the III-V substrate 120 and the waveguides 130a, 130b on the (silicon) substrate 110 based on mode profiles engineered on both sides. The adiabatic coupler is also known and is an interface that provides structures to place co-propagating waveguides in close proximity to facilitate mode evolution to transfer power from one waveguide to another (from one side to another).

Figure 3:
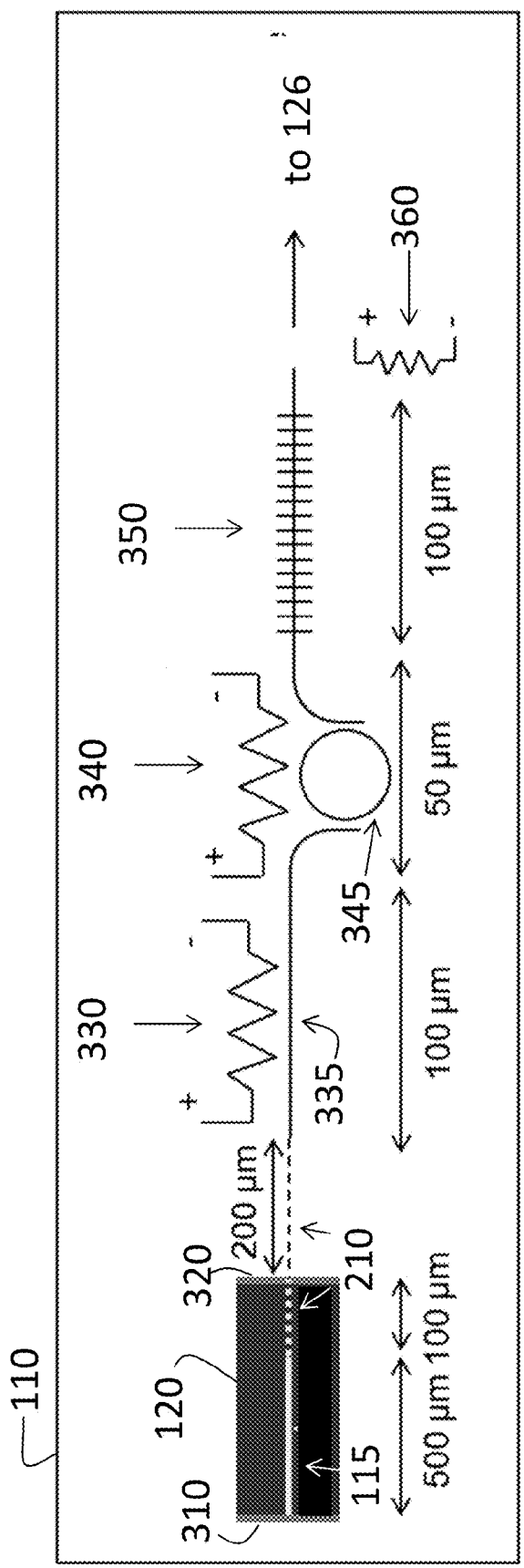
FIG. 3 is a schematic diagram of an external cavity laser used in the gas sensor according to embodiments.

FIG. 3 is a schematic diagram of an external cavity laser 310 used in the gas sensor 100 according to embodiments. The external cavity laser 310 includes the laser 115 and other components that facilitate generation of a specific frequency of interest. As detailed below, the frequency of the laser output is tuned based on changing optical path length (exemplary optical path lengths are shown in FIG. 3). The laser 115 is formed on the III-V substrate 120 along with an optical coupler 210 (e.g., spot size converter). An optical coupler 210 is also on the (silicon) substrate 110. A high reflection (HR) mirror 310 is disposed on one side of the laser 115 on the III-V substrate 120 while an anti-reflection (AR) mirror 320 is disposed on the other side. The light from the coupler 210 on the (silicon) substrate 110 passes through two intra-cavity phase and filter tuner elements (335, 345), that are tuned via two resistive heaters (330, 340). Heat from heater 330 changes the waveguide optical index of a portion 335 of the waveguide 125 and therefore the optical length of that portion 335 of the waveguide, which serves as an intra-cavity phase tuner for the laser. Next, an intra-cavity ring filter 345 provides for single frequency operation. The frequency of the ring filter is adjustable through heater 340. Distributed Bragg reflector (DBR) gratings 350 form the end of the external cavity. The optical distance between the DBR gratings 350 and the HR mirror 310 is therefore adjustable through heaters 330 and 340 in order to adjust the frequency of the light that ultimately reaches the splitter 126. The thermistor 360 measures the average temperature of the substrate 110 and helps adjust the heaters (330, 340), particularly when the ambient temperature changes. According to the embodiment shown in FIG. 2, the III-V substrate 120 may additionally include the detectors 145a, 145b above and below the laser 115 according to the arrangement shown in FIG. 3, for example. An embodiment that includes manufacture of the laser 115 and the detectors 145a, 145b on the III-V substrate 120 may be simplified and highly reproducible.

Figure 4:
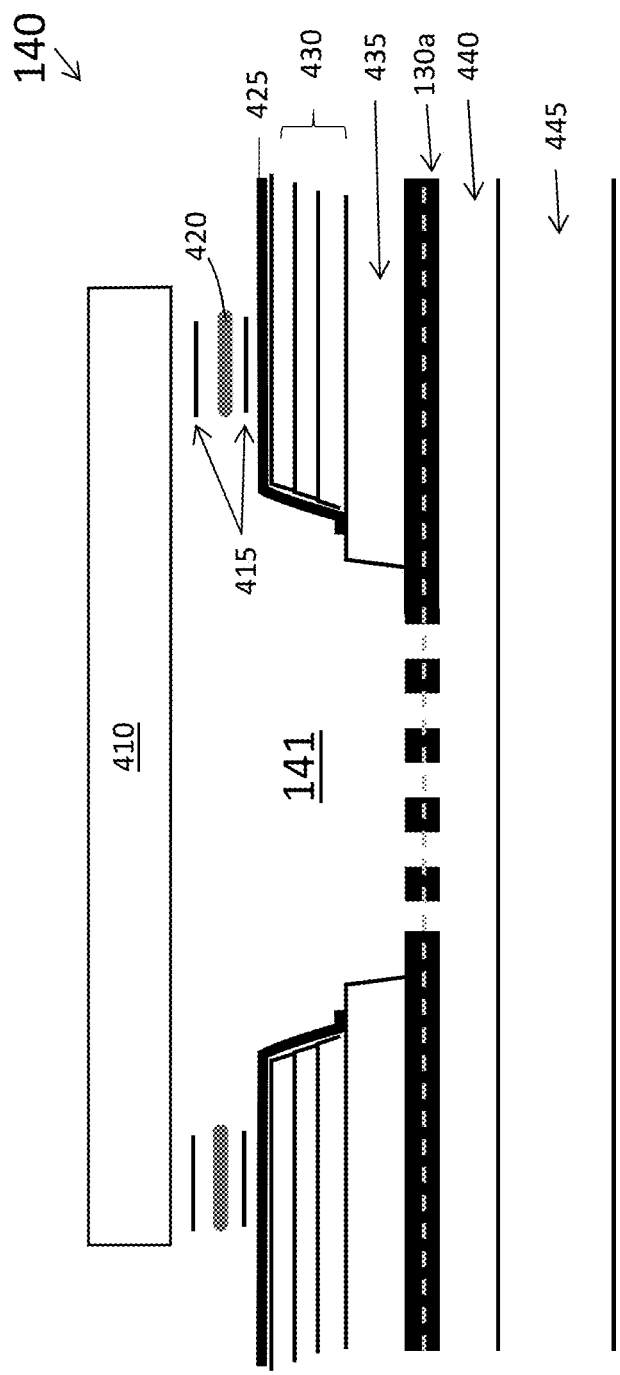
FIG. 4 depicts a cross-sectional view of an exemplary reference cell according to an embodiment.
Figure 5:
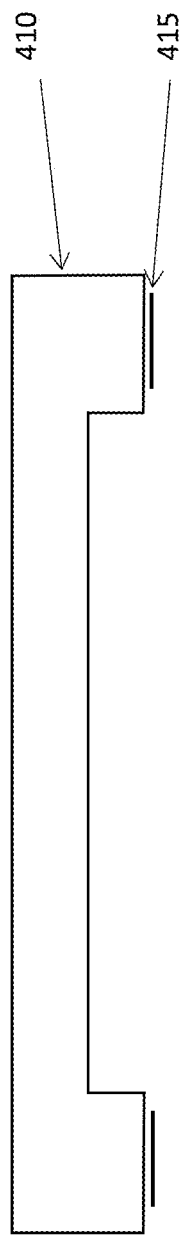
FIG. 5 shows a cross sectional view of an embodiment of the lid of the reference cell according to an embodiment.
Figure 6:
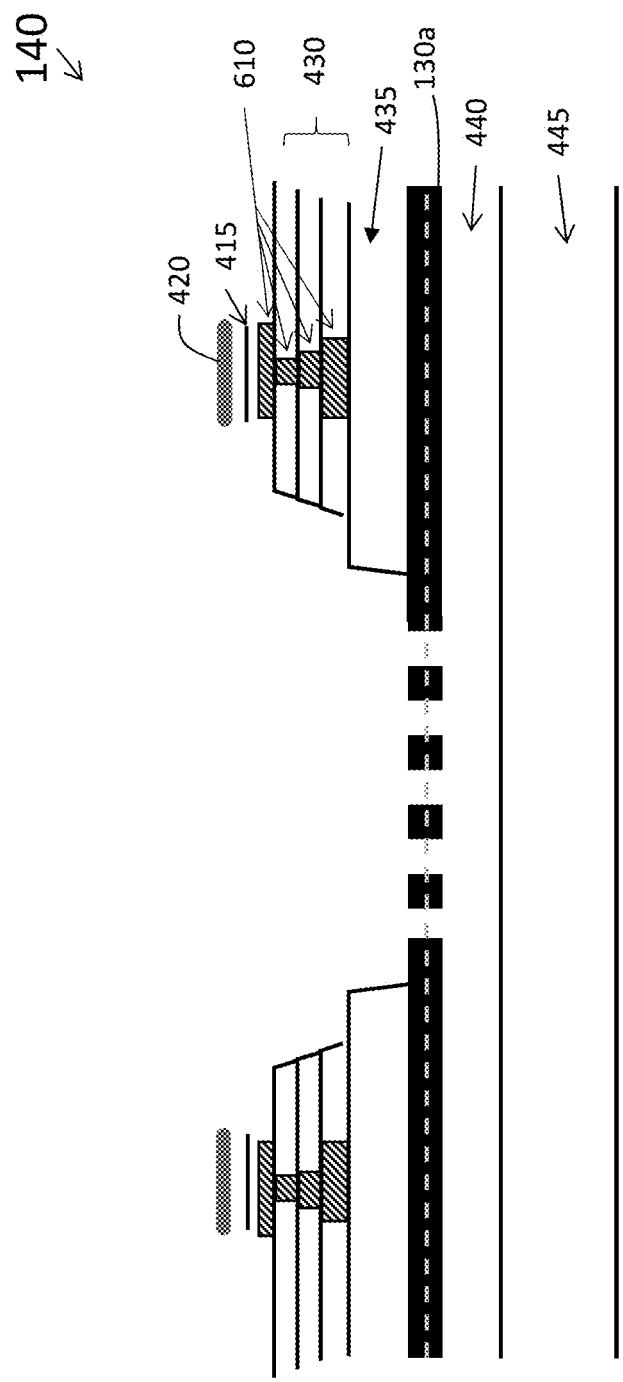
FIG. 6 depicts an exemplary reference cell according to another embodiment.

As noted above, the reference cell 140 is hermetically sealed. This minimizes leakage and diffusion of the reference gas 141 from the reference cell 140 and thereby increases the longevity of the gas sensor 100. FIGS. 4-6 detail the fabrication of the reference cell 140 according to embodiments.

FIG. 4 depicts a cross-sectional view of an exemplary reference cell 140 according to an embodiment. FIG. 4 shows an exploded view so that each layer of the reference cell 140 may be more easily identified. A substrate or handle 445 is formed as a base with a dielectric layer 440 formed above. The substrate material may be silicon or any rigid material such as, for example, other semiconducting material (germanium, III-V semiconductors), or insulators (e.g., ceramic, glass), or metals. The waveguide 130a is formed on the dielectric layer 440. The volume of the cavity of the reference cell 140 is defined by the thickness of dielectric layers 435 and back-end layers 430 shown in FIG. 4 as being formed on each side of the reference cell 140 and the serpentine portion of the waveguide 130a. Dielectric layers 440, 435 may be oxides ($SiO_2$) or other materials that are transparent to the laser light (e.g., silicon nitride ($Si_3N_4$), other glass materials, transparent polymers), because some evanescent fraction of the light travels in this dielectric medium. Because the view in FIG. 4 is a cross sectional view across the middle of the reference cell 140, the dielectric layer 435 and band-end layers 430 formed as continuous layers on each end (in front of and behind the cross section shown in FIG. 4) are not shown. The back-end layers 430 include electrical circuits and are coated with a sealing liner 425. The sealing liner 425 is used to prevent leakage of gas 141 from the cavity of the reference cell 140 over time. Thus, a polymer, which is susceptible to gas diffusion, may be an inadequate choice for the sealing liner 425. Instead, a metal (e.g., aluminum, copper, nickel, titanium) or a dielectric (e.g., silicon dioxide, silicon nitride), a crystal (e.g., silicon), or glass may be used as the sealing liner 425. When the sealing liner 425 is a metal, the sealing liner may be kept some distance (e.g., 1 micron) away from the waveguide 130a. This prevents the evanescent portion of the guided light from interacting with the metal (sealing liner 425), which would attenuate the evanescent portion as a result of the interaction. When the sealing liner 425 is a transparent dielectric, the sealing liner 425 may extend down to the waveguide 130a and even touch the waveguide 130a. The lid 410 is attached to the sealing liner 425 with solder-wettable films 415 on the periphery of each of the lid 410 and sealing liner 425 that sandwich a metal solder 420. The lid 410 may be an impermeable material (e.g., silicon, crystal, glass). The solder-wettable films 415 may include metal films or titanium, chromium, nickel, copper and gold. The solder 420 material may include typical solder metals (tin, silver, gold, indium, bismuth, lead) and may be formed by heating above the solder melting temperature, which may be on the order of 100 to 300 degrees Celsius, in a gas atmosphere that includes the reference gas 141, such as methane. The gas atmosphere may also include an inert gas (e.g., nitrogen, argon) and an oxide removing flux (such as a traditional paste or liquid flux) or a reducing gas (hydrogen or an acid gas such as formic acid gas, for example, either such gas being in small concentration around 5%). When the lid 410 and the substrate or handle 445 are formed of the same material (e.g., silicon), the expansion due to heating the solder to seal the reference cell 140 may be matched such that a tight seal is formed with no gaps.

FIG. 5 shows a cross sectional view of an embodiment of the lid 410 of the reference cell 140 according to an embodiment. The solder-wettable film 415 used to solder the lid 410 to the sealing liner 425 on the back-end layers 430 is also shown. The embodiment of the lid 410 shown in FIG. 5 includes a recess that creates additional volume in the reference cell 140. The increased volume of the reference cell 140, which corresponds with increased volume of the reference gas 141, results in an extended lifetime of the gas sensor 100. Variations on the shape of the lid 140 shown in FIG. 5 are contemplated, and any embodiment of a lid 140 may be used with any embodiment of the other components of the reference cell 140 discussed herein.

FIG. 6 depicts an exemplary reference cell 140 according to another embodiment. While other components of the reference cell 140 are the same among the embodiments shown in FIGS. 4 and 6, the back-end layers 430 of the present embodiment, shown in FIG. 6, include a sealing ring structure 610 rather than a sealing liner 425. The sealing ring structure 610 may be formed with metal guard rings that are connected along the depth of the back-end layers 430 as shown in FIG. 6. As noted above, in addition to the heat noted with reference to FIG. 4, bonding the solder 420 may include the presence of methane, an inert gas, some vapor or traditional flux, and (or alternately) a sequence of gases.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one more other features, integers, steps, operations, element components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated The flow diagrams depicted herein are just one example. There may be many variations to this diagram or the steps (or operations) described therein without departing from the spirit of the invention. For instance, the steps may be performed in a differing order or steps may be added, deleted or modified. All of these variations are considered a part of the claimed invention.

While the preferred embodiment to the invention had been described, it will be understood that those skilled in the art, both now and in the future, may make various improvements and enhancements which fall within the scope of the claims which follow. These claims should be construed to maintain the proper protection for the invention first described.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A gas sensor fabricated on a substrate that includes optical and electronic components, the sensor comprising:
    a laser configured to output light in a range of wavelengths within a waveguide;
    a splitter configured to split the light output by the laser to a reference waveguide and to a detection waveguide;
    the reference waveguide configured to expose the light to a reference gas and output a reference light, wherein the reference light exhibits a change in intensity from the light at wavelengths corresponding with an absorption spectrum of the reference gas;
    a reference cell configured to hermetically seal the reference gas and house the reference waveguide;
    the detection waveguide configured to expose the light to ambient gas; and
    first and second optical detectors configured to receive light output from the reference waveguide and the detection waveguide, respectively, wherein the ambient gas is identified based on outputs of the first detector and the second detector.

2. The sensor according to claim 1, further comprising a III-V die on the substrate, wherein the laser is formed on the III-V die.

3. The sensor according to claim 2, wherein the first detector and the second detector are also formed on the III-V die.

4. The sensor according to claim 2, further comprising optical couplers on the III-V die and on the substrate.

5. The sensor according to claim 1, wherein the reference cell includes back-end layers and a dielectric layer that define a volume of a cavity in which the reference gas is housed.

6. The sensor according to claim 5, further comprising a sealing liner over the back-end layers.

7. The sensor according to claim 5, further comprising a sealing ring structure within the back-end layers.

8. The sensor according to claim 5, further comprising a cap soldered above the back-end layers.

9. The sensor according to claim 1, wherein the laser is part of an external cavity laser configured to tune the range of wavelengths of the light output by the laser based on adjusting an optical path length.

10. The sensor according to claim 9, wherein the laser is tuned based on an absorption wavelength of the reference gas.

\* \* \* \* \*